US00PP29722P2

(12) United States Plant Patent
Van Dijk

(10) Patent No.: US PP29,722 P2
(45) Date of Patent: Oct. 2, 2018

(54) ***ANTHURIUM* PLANT NAMED 'ANTHIOXI'**

(50) Latin Name: ***Anthurium andraeanum* L.**
Varietal Denomination: ANTHIOXI

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,476

(22) Filed: Jun. 15, 2017

(51) Int. Cl.
*A01H 5/02* (2018.01)

(52) U.S. Cl.
USPC ..... Plt./365

(58) Field of Classification Search
USPC ..... Plt./365
CPC ... A01H 5/02; A01H 5/00; A01H 5/12; A01H 6/00
See application file for complete search history.

(56) References Cited

U.S. PATENT DOCUMENTS

PP27,137 P3 * 9/2016 Van Dijk ..... Plt./365

OTHER PUBLICATIONS

Upov Pluto Plant Variety Database May 5, 2018 for *Anthurium* Anthioxi, retrieved on May 8, 2018, retrieved from the internet at https://www3.wipo.int/pluto/user/en/index.jsp, one page. (Year: 2018).*

EU Community Plant Variety Rights Application No. 2016/1484, Application n°A201601240, filed Jun. 17, 2016, 8 pages.

EU Community Plant Variety Office Official Gazette, Apr. 2016, Aug. 15, 2016, cover page and pp. 28, 47.

* cited by examiner

*Primary Examiner* — June Hwu

(74) *Attorney, Agent, or Firm* — Jondle & Associates, P.C.

(57) ABSTRACT

A new *Anthurium* cutflower plant named 'ANTHIOXI' particularly distinguished by having very shiny and strongly blistered, green, oblong-cordate and very durable spathes that retain the original color for a very long period of time, dark green and elliptical cordate, durable leaves, white spadix with green tip, early and rich flowering continuously throughout the year and a plant height of 60.0 cm to 70.0 cm, is disclosed.

3 Drawing Sheets

Genus and species: *Anthurium andraeanum* L.
Variety denomination: 'ANTHIOXI'.

BACKGROUND OF THE NEW PLANT

The present invention comprises a new and distinct variety of *Anthurium*, botanically known as *Anthurium andraeanum* L., and hereinafter referred to by the variety name 'ANTHIOXI'. The new *Anthurium* plant is a product of a planned breeding program conducted by the inventor in Bleiswijk, the Netherlands. The objective of this breeding program was to create a new cutflower plant with very shiny, green, oblong-cordate leaves and very durable spathes.

The new variety originated from a cross-pollination made in November 2000 in Bleiswijk, The Netherlands. The female parent was a light green *Anthurium* cutflower plant designated '1535-02' (unpatented), and the male parent was a cream *Anthurium* cutflower plant designated '00-0271' (unpatented).

A single plant was selected from the progeny of the stated cross in January 2003 and has been asexually reproduced repeatedly by meristem tissue culture in Bleiswijk, The Netherlands over a 9-year period. The present invention has been found to retain its distinctive characteristics through successive asexual propagations.

Plant Breeder's Rights for this variety have been applied for in the European Union on Jun. 17, 2016. 'ANTHIOXI' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Very shiny and strongly blistered, green, oblong-cordate spathe;
2) White spadix with green tip;
3) Green, elliptical cordate leaves; and
4) Veins of the spathe become red-brown while aging.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 60-week old plant grown in a greenhouse in Bleiswijk, The Netherlands in May 2017. Colors in the photographs may differ from the color values cited in the detailed botanical description, which accurately describe the actual colors of the new variety.

DESCRIPTION OF THE NEW VARIETY

Figure 1:
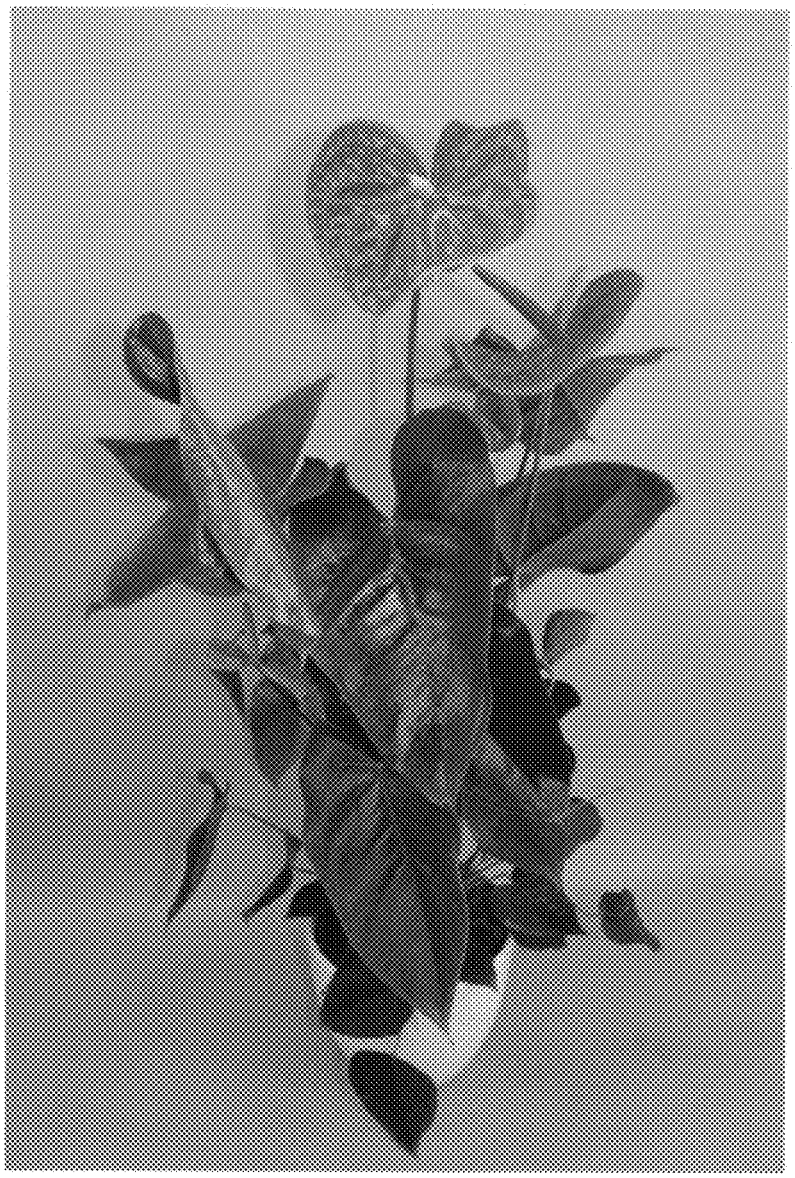
FIG. 1 shows the overall plant habit, including blooms and foliage.
Figure 2:
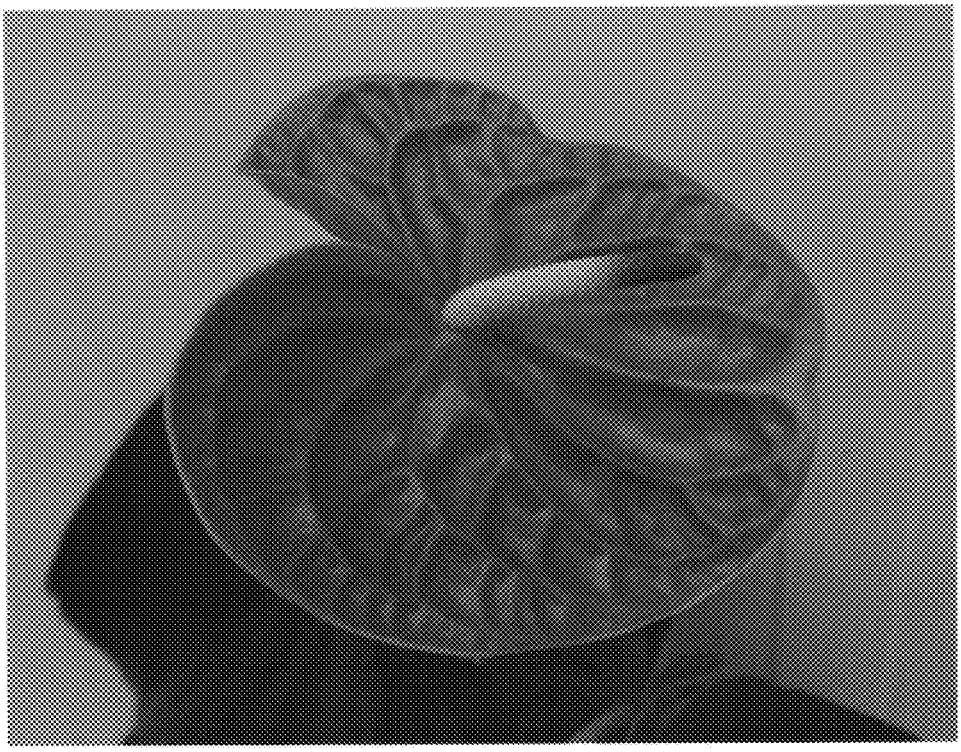
FIG. 2 shows a close-up of the mature spathe.
Figure 3:
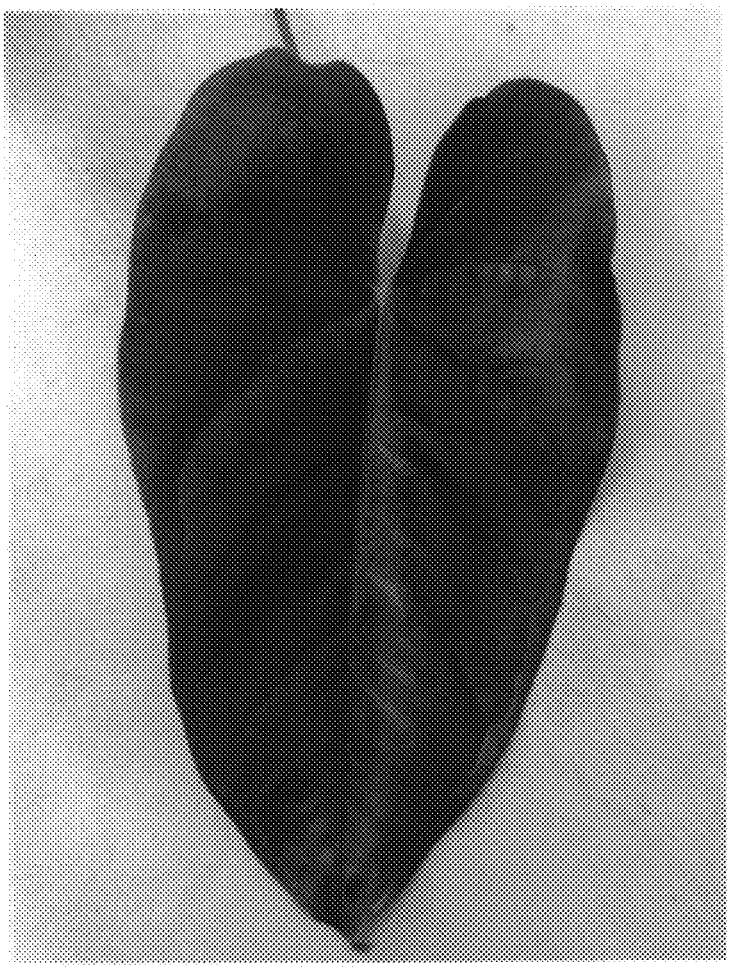
FIG. 3 shows a close-up of the upper leaf blade surface.

The following detailed description sets forth the distinctive characteristics of 'ANTHIOXI'. The data which define these characteristics were collected from asexual reproductions carried out in Bleiswijk, The Netherlands. The plant history was taken on 60-week old plants which were planted from tissue culture in 17 centimeter (diameter) pots and grown in a glass greenhouse between 19° C. and 24° C. Observations were made in May 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHIOXI'.

Parentage:

*Female parent*.—*Anthurium* plant '1535-02' (unpatented).

*Male parent*.—*Anthurium* plant '00-0271' (unpatented).

Plant:

*Propagation*.—Meristem tissue culture.

*Root description*.—Fleshy-creamy colored roots with small hairy lateral roots having yellow colored root tips.

*Time to produce a finished flowering plant*.—55 to 65 weeks after planting in a 17 cm (diameter) pot.

*Growth habit*.—Herbaceous perennial.

*Height* (*measured from soil, including inflorescence*).—60.0 cm to 70.0 cm.

*Width* (*measured from leaf tips*).—50.0 cm to 60.0 cm.

Leaves:

*Immature leaves*.—Length: 22.0 cm to 25.0 cm. Width: 13.0 cm to 16.0 cm. Color: Upper surface: RHS 146A. Lower surface: RHS 146B. Texture (both upper and lower surfaces): Shiny.

*Mature leaves*.—Length (fully expanded): 30.0 cm to 33.0 cm. Width: 16.0 cm to 19.0 cm. Shape: Elliptical cordate. Apex: Acuminate. Base: Cordate. Leaf blade angle with the petiole: Between 95 degrees and 115 degrees. Leaf margin: Entire. Color: Upper surface: RHS 147A. Lower surface: RHS 147B. Texture (both upper and lower surfaces): Shiny. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Present. Arrangement: Leaf blade has two lobes extending past the petiole. The lobes are non-touching. Length of lobes of mature leaf blades: 7.5 cm to 8.5 cm. Width of lobes of mature leaf blades: 8.0 cm to 9.0 cm. Distance from petiole/leaf junction to highest point on lobes of mature leaf: 0.5 cm to 1.5 cm.

*Petiole*.—Cross-section: Round. Diameter: 0.4 cm to 0.6 cm. Length: 40.0 cm to 50.0 cm for a mature leaf size. Color: Mature leaf: RHS 144A. Immature leaf: RHS 144B. Cataphyll color surrounding the petiole: Outside: RHS 144B. Inside: RHS 144C.

*Geniculum*.—Length: 2.0 cm to 2.5 cm. Width: 0.5 cm to 0.6 cm. Color: RHS 144C.

Inflorescence:

*Arrangement*.—Single.

*Flowering habit* (*length of flowering season*).—Continuous.

*Number of inflorescences per plant*.—The plant produces 4 to 6 flowers in the period of one year. Ripe flowers are harvested, so only one flower is present on the plant at a time.

*Fragrance*.—Absent.

*Longevity of flowers as a cut flower*.—35 to 45 days.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 90 degrees and 110 degrees; the spathe stands on a wiry peduncle about 9.0 cm to 14.0 cm above the foliage. The spathe is positioned at the same level to far above the foliage.

*Shape*.—Oblong cordate.

*Apex*.—Mucronate.

*Base*.—Cordate.

*Texture*.—Very shiny and strongly blistered.

*Margin*.—Entire.

*Size*.—Length: 14.0 cm to 16.0 cm. Width: 15.0 cm to 16.0 cm.

*Lobes*.—Present.

*Arrangement*.—The spathe has two lobes extending past the peduncle. The lobes are non-touching. Length: 5.5 cm to 6.5 cm. Width: 8.0 cm to 9.0 cm.

*Color*.—Just fully open: Upper surface: RHS 144A. Lower surface: RHS 144B. This green color remains for a very long period, at least more than 35 days after opening. Fading inflorescence: Yellow-green (RHS 146C) with red overcolor and middle vein (RHS 184B); slightly greenish-yellow (RHS 153A) at the margin.

Peduncle:

*Shape*.—Erect.

*Cross-section*.—Round.

*Length*.—54.0 cm to 57.0 cm.

*Diameter*.—0.4 cm to 0.6 cm.

*Color*.—RHS 144A.

Flowering time:

*General*.—One small rooted untreated tissue culture plant of 4.0 cm tall will flower, depending on season, after 30 to 35 weeks.

Spadix:

*Size*.—Length: 8.0 cm to 9.0 cm (depending on flower size). Width (at apex): 0.5 cm to 0.7 cm. Width (at base): 0.7 cm to 0.9 cm.

*Shape*.—Columnar.

*Angle from spadix tip to peduncle*.—130 degrees to 150 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 146A. Mature: RHS 155B. Ages to: RHS 146C.

Flowers:

*Quantity per spadix*.—250 to 350.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: Many. Length: Less than 0.01 cm. Color: RHS 158C.

*Style*.—Not observed.

*Stigma*.—Shape: Ovoid. Diameter: Less than 0.01 cm. Color: RHS 158C.

*Ovary*.—Rarely visible.

*Ovary color*.—Not measured.

Fruit and seed set: None observed to date.

COMPARISON WITH PARENTAL AND COMMERCIAL VARIETIES

'ANTHIOXI' differs from the female parent plant '1535-02' (unpatented) in that 'ANTHIOXI' has green, oblong-cordate shaped spathes with non-touching lobes, whereas '1535-02' has light green, cordate shaped spathes with touching lobes. Additionally, 'ANTHIOXI' has green (RHS 146A) immature spadix, maturing to white (RHS 155B) whereas '1535-02' has green (RHS 146C) immature spadix, maturing to white (RHS 158B).

'ANTHIOXI' differs from the male parent plant '00-0271' (unpatented) in that 'ANTHIOXI' has green, oblong-cordate spathes with non-touching lobes, whereas '00-0271' has cream with pink blush, cordate shaped spathes with overlapping lobes. Additionally, 'ANTHIOXI' has green immature spadix, maturing to white, whereas '1535-02' has orange-red immature spadix, maturing to white.

'ANTHIOXI' differs from similar commercial variety 'ANTHINFAM' (U.S. Plant Pat. No. 27,137) in that 'ANTHIOXI' has elliptical cordate leaves, whereas 'ANTHINFAM' has ovate leaves. Additionally, 'ANTHIOXI' has fewer flowers per spadix than 'ANTHINFAM'.

'ANTHIOXI' differs from similar commercial variety 'Midori' (unpatented) in that 'ANTHIOXI' has green (RHS 144A) spathes, whereas 'Midori' has green (RHS 144B) spathes. Additionally, the angle of the spadix tip with the peduncle of 'ANTHIOXI' is larger than that of 'Midori'.

I claim:

1. A new and distinct variety of *Anthurium* plant named 'ANTHIOXI', substantially as illustrated and described herein.

* * * * *